(12) United States Patent
Illi

(10) Patent No.: US 6,214,008 B1
(45) Date of Patent: Apr. 10, 2001

(54) BIODEGRADABLE OSTEOSYNTHESIS IMPLANT

(75) Inventor: Oskar E. Illi, Schwerzenbach (CH)

(73) Assignee: White Spot AG, Baar (CH)

( * ) Notice: Subject to any disclaimer, the term of this patent is extended or adjusted under 35 U.S.C. 154(b) by 0 days.

(21) Appl. No.: 09/403,235

(22) PCT Filed: Apr. 8, 1998

(86) PCT No.: PCT/CH98/00133

§ 371 Date: Oct. 15, 1999

§ 102(e) Date: Oct. 15, 1999

(87) PCT Pub. No.: WO98/46289

PCT Pub. Date: Oct. 22, 1998

(30) Foreign Application Priority Data

Apr. 16, 1997 (CH) ........................................ 884/97
Apr. 1, 1998 (CH) ........................................ 780/98

(51) Int. Cl.[7] .................................................. A61B 17/58

(52) U.S. Cl. ........................... 606/77; 606/76; 623/16.11; 623/11.11

(58) Field of Search .............................. 606/76, 77, 230, 606/71; 623/11.11, 16.11, 23.58, 23.56, 901, 926; 525/415, 408, 409

(56) References Cited

U.S. PATENT DOCUMENTS

| 4,655,777 | * | 4/1987 | Dunn et al. ................. 623/16.11 |
| 4,968,317 | * | 11/1990 | Tormala et al. ................. 606/77 |
| 5,433,751 | * | 7/1995 | Christel et al. ................. 606/77 |
| 5,470,829 |   | 11/1995 | Prisell et al. . |
| 5,522,841 | * | 6/1996 | Boby et al. ................. 606/230 |
| 5,522,895 | * | 6/1996 | Mikos ................. 606/77 |
| 6,077,267 | * | 6/2000 | Huene ................. 60/77 |

FOREIGN PATENT DOCUMENTS 0 206 801  12/1986  (EP) .
WO 96/00592 * 1/1996 (EP) ........................................ 606/77

OTHER PUBLICATIONS

Froger–Gaillard et al.:*Production of Insulin–Like Growth Factors And Their Binding Proteins By Rabbit Articular Chondrocytes: Relationships With Cell Multiplication*, Endocrinology, vol. 124, No. 5, pp. 2365–2372 (1989).

T.K. Sampath.;*Recombinant Human Osteogenic Protein–1 (hOP–1) Induces New Bone Formation In Vivo With A Specific Activity Comparable With Natural Bovine Osteogenic Protein And Stimulates Osteoblast Proliferation And Differentiation In Vitro*, J. Biol Chem. vol. 267, No. 28, pp. 20352–20362 (1992).

Diana L. Griffith et al.:*Three–dimensional structure of recombinant human osteogenic protein 1: Structural paradigm for the transforming growth factor beta superfamily*, Proceedings of the National Academy of Sciences, pp. 878–883, vol. 93, No. 2, 1996.

Eichi Tsuruga et al.: *Pore Size of Porous Hydroxyapatite as the Cell–Substratum Controls BMP–Induced Osteogenesis 1*, J. Biochem., vol. 121, pp. 317–324 (1997).

(List continued on next page.)

*Primary Examiner*—Pedro Philogene
(74) *Attorney, Agent, or Firm*—Pauley Petersen Kinne & Fejer

(57) ABSTRACT

An osteosynthetic implant for a mechanical connection of fractured elements, made of a polymeric biodegradable base material, for use in reconstructive osteosynthesis. An active ingredient assists the regeneration of bone tissue in a fracture area and acts together with the implant to assist growth in the fracture area, so that the mechanical load-bearing capability of the healing fracture increases faster or at least as fast as the load-bearing capability biodegradable implant decreases when decomposing.

18 Claims, 2 Drawing Sheets

OTHER PUBLICATIONS

Hossein Zia et al.: *Why Infusion and Not Microcapsules or Other Controlled Release Methods?*, Encapsulation and Controlled Release, pp. 117–122, Thomas Graham House, Cambridge, 1996.

D.E. Cutright and E.E. Hunsuck: *The repair of fractures of the orbital floor using biodegradable polylactic acid*, Journal of Oral Surgery, vol. 33, 28–34, Jan. 1972.

E. Wintermantel and S–W Ha, *Biokompatible Werkstoffe and Bauweisen*, Biocompatible Materials and Structural Forms, 315–323, ISBN 3–540–59405–1, Springer–Verlag, Berlin Heidelberg 1996.

Froger–Gaillard et al.:*Production of insulin–like growth factors and their binding proteins by rabbit articular chondrocytes: relationships with cell multiplication*, Endocrinology 124, p. 1, 1989.

T.K. Sampath et al.: *Recombinant human osteogenic protein–1 (hOP–1) induces new bone formation in vivo with a specific activity comparable with natural bovine osteogenic protein and stimulates osteoblast proliferation and differentiation in vitro*, J. Biol Chem. 267, p. 1, p.1 and p. 2, 1992.

Diana L. Griffith et al.: *Three–dimensional structure of recombinant human osteogenic protein1: Structural paradigm for the transforming growth factor beta superfamily*, Proceedings of the Natlional Academy of Sciences, p. 1, vol. 93, No. 02, 1996.

* cited by examiner

BIODEGRADABLE OSTEOSYNTHESIS IMPLANT

BACKGROUND OF THE INVENTION

1. Field of the Invention

This invention relates to a biodegradable osteosynthesis implant constructed of a polymeric biodegradable base material with active ingredients that aid regeneration of bone tissue in a fracture area.

2. Description of Prior Art

Metallic implants have been used in medicine for more than 200 years for fixation of broken bones. Success was achieved in the last decades with the selection of suitable compatible metal alloys to optimize the mechanical load-bearing capacity, and above all the tissue tolerance of these implants so that corrosion and rejection reactions rarely occur. Complications because of the metallic implants can arise in the course of X-ray and tomographic diagnostic processes. One main disadvantage associated with conventional implants is that metallic implants cannot remain in the human body over an unlimited time. It is therefore necessary to perform a second surgical procedure for removing the implant after the fracture has healed. This not only involves another stress for the patient, but also results in considerable costs for the second surgical procedure and the necessary second stay of a patient in a hospital. In addition, direct and indirect costs result from loss of work and after-treatment during the second healing of the wound. Therefore efforts have been made over a considerable period of time to replace the metallic materials with biodegradable polymers so that removal of the implant after healing of the fracture is no longer necessary.

The use of a biodegradable plate in connection with osteosynthesis was first described by D. E. Cutright and E. E. Hunsuck in the Journal of Oral Surgery, Volume 33, pages 28 to 34 (1972).

In developing novel biodegradable implants, it has been a goal to replace metallic implants. Thus the implant had to fix the bone fragments in place and support the mechanical forces acting on the bone.

However, implants made of absorbable polyesters have inferior mechanical load-bearing capabilities when compared to implants made of metal. Although it was possible using suitable production methods, for example injection molding methods, and using optimized material mixtures to produce implants, for example fiber-reinforced implants, which could resist great tensile stresses, the flexible strength of such workpieces is relatively low and far below that of metal implants. A range of applications of biodegradable osteosynthesis materials is limited to lightly stressed, rapidly healing fractures. Such fractures can occur, for example, on the skull, such as a roof of the skull, a cheek bone or an upper jaw.

SUMMARY OF THE INVENTION

As shown in FIGS. 1a and 1b, an increase in the stability of the bone and a decrease in the stability of the implant are two dynamically occurring processes, which are expressed in two oppositely extending sigmoidal curves. Ideally, these curves are superimposed on each other in such a way that the stability of the implant decreases to the same extent as the stability of the bone increases again. The hypothetical course of the healing of the fracture with only the employment of a biodegradable osteosynthesis implant is represented in FIG. 1a, such as occurs for example, in treatment of the above described fractures in the skull area. At the time equal to zero, the implant must be able to withstand the total mechanical stress, and the loss of mechanical stability, less a defined mechanical stability reserve, may advance no faster than it can be compensated by the increase in the stability of the healing bone tissue.

It can also be seen from FIG. 1a that the loss of stability of the implant cannot be equated with its decomposition or loss of mass. The implant loses mechanical stability much faster by various physical and chemical processes, for example, by swelling, than it loses mass by abrasion and degradation.

Generally an implant not only must fix the bone fragments in place during the healing of the fracture, but must also support the mechanical forces acting on the bone. The implant can be relieved from supporting the mechanical forces acting on the bone to a large extent by means of an external support such as plaster, splints or an external fixation device, and merely needs to assure the fixation of the fragments. This quite decisively increases the application range of biodegradable polymer implants.

As shown in FIG. 1b, the biodegradable and absorbable implant only needs to fix the bone fragments in a defined position with respect to each other until the bone material newly formed between them can take up this function again, and the additional fixation becomes unnecessary. But the mechanical stresses acting on the broken bone are supported by the external stabilizing device until the healing bone has regained a percentage of sufficient size of its mechanical properties, so that additional stabilization is no longer required. This does not mean that the bone must already have regained its full mechanical load-bearing capacity when the external stabilization means is removed. An affected area is commonly immobilized for an extended period of time, and the reduced muscle activity leads to loss of muscle and reduced mobility. To regain these, it is necessary to perform time-intensive and cost-intensive therapies after the removal of the external stabilizing means.

Polylactide (PLA), polyglycolide (PGA), poly((ε-caprolcatone) (PCL), poly (β-hydroxybutyrate) (PHB) or poly(p-dioxanone) (PDS) and their copolymers are decomposed in the body into the respective degradation products and can either flow into the body metabolism, or can be precipitated by the body through the urine or through breathing.

Polylactide (PLA) and polyglycolide (PGA) and their copolymers are decomposed by hydrolysis. Since the amorphous areas of partially crystalline PLA degrade more rapidly than the crystalline areas, irritation and inflammation because of the crystallites can occur after disintegration of the implant in the surrounding tissue, as described by E. Wintermantel and S-W Ha, "Biokompatible Werkstoffe und Bauweisen," in Biocompatible Materials and Structural Forms, Springer publications, Berlin 1996. A second cause of complications can be from the acid hydrolysis products of the implant. The acid degradation products are removed from the interior of the implant essentially more slowly than from its surface, which leads to the amassing of acid decomposition products and an increasing acceleration of the decomposition by auto-catalytically acting carboxyl groups. If at a later time during the decomposition the remaining outer wall of the implant breaks, a sudden release of the acid products and therefore a sudden pH drop in the surrounding tissue can occur, which can also lead to inflammatory reactions.

The speed of bone healing can be accelerated by various growth factors (GFs). Soluble, low-molecular proteins, such as the insulin-like growth factors (IGFs) have been known for some time for their local action on the growth of cartilage and bones, as set forth by Canalis, E. and L. G. Raisz, in Endocr. Rev. 4; pages 62 to 77 (1983). The same authors have proven a positive effect of IGF on the bone-DNA synthesis in periosteal and non-periosteal bones.

One advantage of using IFG in the treatment of wounds and fractures is that up to now IFG has not shown any known relationship with oncogenes.

Two insulin-like growth factors are commercially offered. IGF-1 (also known as Somatomedin C) is a basic polypeptide having 70 amino acids, and having a molecular weight of 7649 D. Inter alia, IGF-1 stimulates the insertion of proteoglycan in the cartilage by means of chondrocytes, as set forth by Froger-Graillard et al., in Endocrinology 124; pages 2365 to 2372 (1989), and in addition the synthesis of DNS, RNS and proteins. The slightly acid polypeptide IGF-2, like IGF-1, has four domains and has a molecular weight of 7471 D. IGF-2 has 64 amino acids. IGFs are mainly dependent on growth hormones (Somatotropin; GH). IGF-1 is preponderantly active in adults, while IGF-2 is the main growth factor of the fetus.

Several active ingredients are known from the group of transforming growth factors (TGFs), which act to stimulate growth and aid in the healing of wounds. The proteins known as bone morphogenetic protein (BMP) can induce ectopic osteogenesis. Sampath et al., J.Biol.Chem. 27; pages 20352–62 (1992) have shown for recombinant human oesteogenetic protein-1 (hoP-1; BMP-2a), that it stimulates bone formation in vivo in the same way as the osteoblast proliferation and differentiation in vitro. D. L. Griffith et al., Proc.Natl.Acad.Sci. Biophysics 93(2); pages 878 to 883 (1996) describes the three-dimensional structure of osteogenic protein 1 (OP1; BMP-7), which can induce bone formation in vivo.

Of the BMPs, which are members of the TGF beta super-family, BMP-4 and BMP-7 are available as recombinant proteins in addition to BMP-2.

In vivo, purified recombinant BMPs appear to be only capable of inducing osteogenesis if they occur linked to suitable support materials or carriers, as set forth by E. Tsuruga et al., in J. Biochem. 121; pages 317 to 324 (1997).

At present, the use of recombinant human BMP-2 (rhBMP-2) and suitable carrier materials is tested in clinical studies by the Genetics Institute® company for accelerating and assuring the healing of bone fractures and bone defects. Similar to the collagen described in European Patent Reference EP-A-0 206 801, the carrier materials are intended to be used in place of bone material of a body (auto graft) as position saver and frame for the bone tissue being newly formed. The collagen claimed in European Patent Reference EP-A-0 206 801 has a very good tissue affinity and acts as a carrier material for BMP. However, the collagen preparations only act as carriers for the growth factors and do not take on a function for stabilizing the break or fixing the bone fragments in place.

It is one object of this invention to combine the positive clinical aspects of bio-absorbable implants with those of growth factors, and to minimize possible negative effects of bio-absorbable implants.

This object is attained by an implant having the characteristics set forth in the claims, with the combining effects of more rapid growth in a fracture area, which permits an implant of lower volume.

BRIEF DESCRIPTION OF THE DRAWINGS

This invention can be better understood when the specification is read in view of the drawings, wherein.

DESCRIPTION OF PREFERRED EMBODIMENTS

Figure 1A:
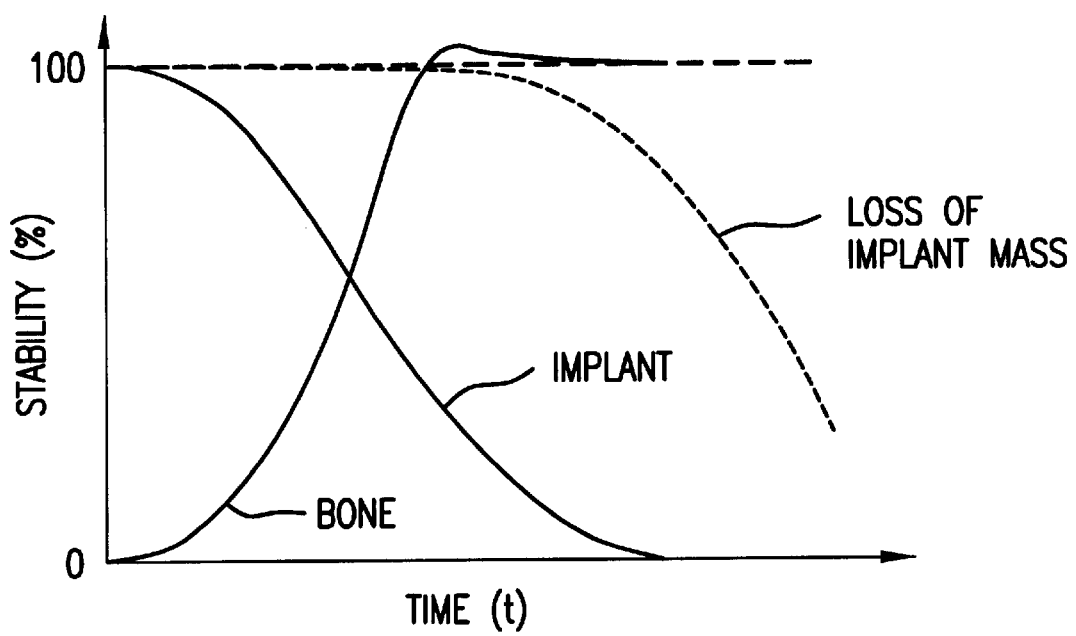
FIG. 1a is a graphical representation showing two curves, one representing a stability of an implant over time and another representing a stability of a bone over time, according to theory.
Figure 1B:
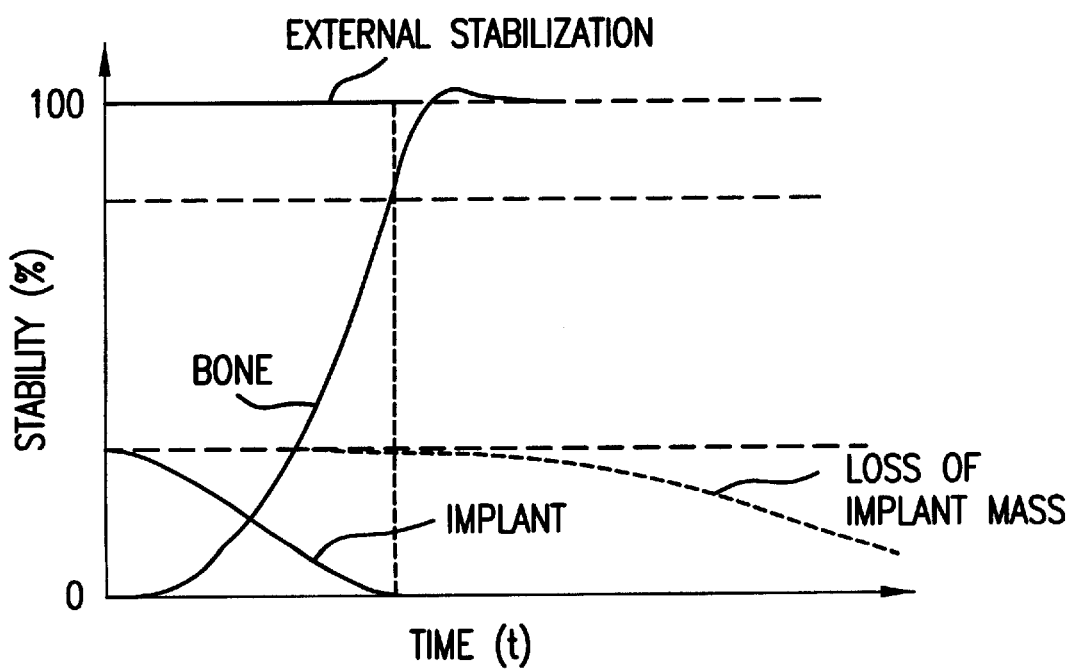
FIG. 1b is a graphical representation showing two curves, one representing a stability of an implant over time and another representing a stability of a bone over time.

The growth factors (GF), which can be employed with this invention, are members of the group of epidermal growth factors (EGF) or of insulin-like growth factors (IGF) or of transforming growth factors beta (TGF-beta) or of the fibriloplast growth factors (FGF). It is also possible to employ suitable combinations of two or more of these growth factors. Many of the above growth factors are commercially available as freeze-dried powders which are converted into one of the following formulations for producing implants in accordance with this invention:

a) Into a solution with a suitable solvent, for example water or 0.1M acetic acid for IGF, wherein concentrations of 1 to 10 ng/ml are advantageous;

b) Deposited in a lycogel or a xerogel;

c) Encapsulated or deposited in biodegradable material, wherein the encapsulation of the GF in micro-capsules made of a suitable biodegradable material, such as polylactide, can be performed for example by means of "in water drying" of w/o/w emulsions. Massive microspheres can be produced from a GF-polymer-solvent mixture, for example by means of "spray-drying".

If the GF is to be introduced into large polymer bodies, this can be done by admixing the GF to the polymer material prior to or during the extrusion process while producing bars or tape-shaped extrudates at low temperatures, or later on by means of an infusion technique such as described by H. Zia et al. in "Encapsulation and Controlled Release", Thomas Graham House, Cambridge, pages 117 to 130 (1996);

d) Covalently linked to carrier proteins or other carrier materials;

e) As a mixture with suitable inactive ingredients; and f) As a pure freeze-dried powder.

All of the above mentioned formulations are well documented and can be found in textbooks, such as, for example: D. R. Karsa and R. A. Stephenson, "Chemical Aspects of Drug Delivery Systems", Thomas Graham House, Cambridge (1996); or D. R. Karsa and R. A. Stephenson, "Encapsulation and Controlled Release", Thomas Graham House; or the Journal of Controlled Release of Elsevier Science; or the product information of various suppliers, for example SIGMA-ALDRICH® or PROMEGA™.

The heat stability of all possible growth factors, except for EGF, is very limited, both in solution or freeze-dried. In accordance with the conventional state of the art, process temperatures above 100° are required, for example in connection with an injection molding process, in order to obtain implants with the desired mechanical properties. A direct admixture of the growth factors to the polymers prior to or during the production of the implant therefore is not useful.

Various methods have been developed for being able to charge the finished implants with GFs formulated in accordance with the above described methods:

a) Covalent binding of the GFs to the surfaces of the polymer material of the implant. To optimize the deposition process, the surfaces can be pre-treated, for example by means of "plasma treatment", such as described by H. Thissen et al. in 1996 during the international symposium on "biodegradable materials" in Hamburg;

b) Application of a GF-containing film layer of polymer material. This can take place either by dipping the implant into a polymer-GF solution, or by coating with or enveloping the implant in a pre-produced polymer-GF film;

c) Placement in hollow spaces or recesses of the implant is primarily suitable for microscopic or macroscopic polymer-GF mixtures or GF gels. For example, once screwed into the bone, the internal diameter of a hollow screw can be filled with an interlocking polymer-GF rod; and d) Adhesives.

The implants produced in this manner can have all embodiment shapes customary for osteosynthesis implants. Advantageous shapes are plates, bandages, fabrics or other flat or rod-shaped elements. Furthermore, connecting elements in the shape of screws, rivets, pins, nails, spiking wires or hoops are produced in accordance with the above described methods.

In addition to the growth factors placed into or on the implant, growth factors which are directly introduced into the fracture area can work together with the implant. To this end, the growth factors present in one of the above formulations a) to f) are brought into an injectable form and are directly injected into the area of the fracture or its immediate vicinity.

In a further advantageous embodiment of this invention, the biodegradable implant can be present spatially separated from the growth factors. In this case the implant is free of growth factors and the growth factors are exclusively present in the injectable formulation. The growth factors which are injected directly into the area of the break or its immediate vicinity act together in an analogous manner with the above described biodegradable osteosynthesis implants, which are free of growth factors.

Figure 2A:
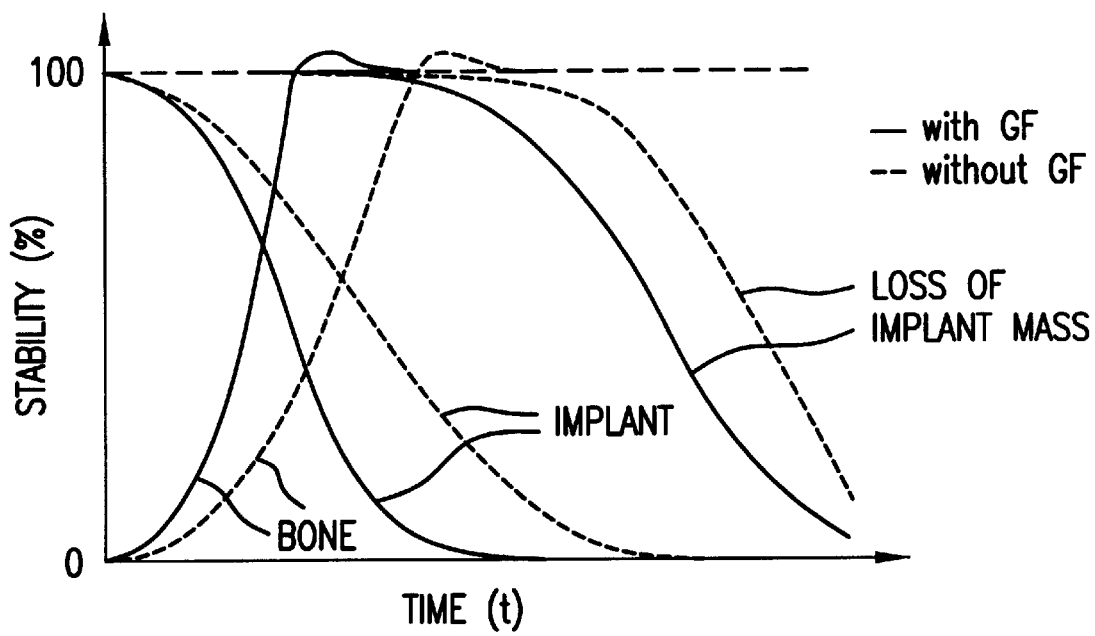
FIG. 2a is a graphical representation showing different curves identifying stability as a function of time, as related to a healing process of a fracture when using an implant in accordance with this invention.

The healing process of a fracture when using an implant in accordance with this invention and the associated growth factors are shown in FIG. 2a. The solid line shows the accelerated chronological course of the formation of new bone, or respectively the increase of the mechanical load-bearing capacity of the healing bone. The slower increase without the employment of growth factors is represented by the dashed line. Although at the time equal to zero the implant must still take on the full mechanical load, it can be made of materials which can be decomposed more rapidly, since it has to bear this load for a much shorter period of time. The conversion of amorphous polymer material into crystallites is also reduced by the shortened presence of the implant in the body, which in turn leads to improved tissue compatibility.

Figure 2B:
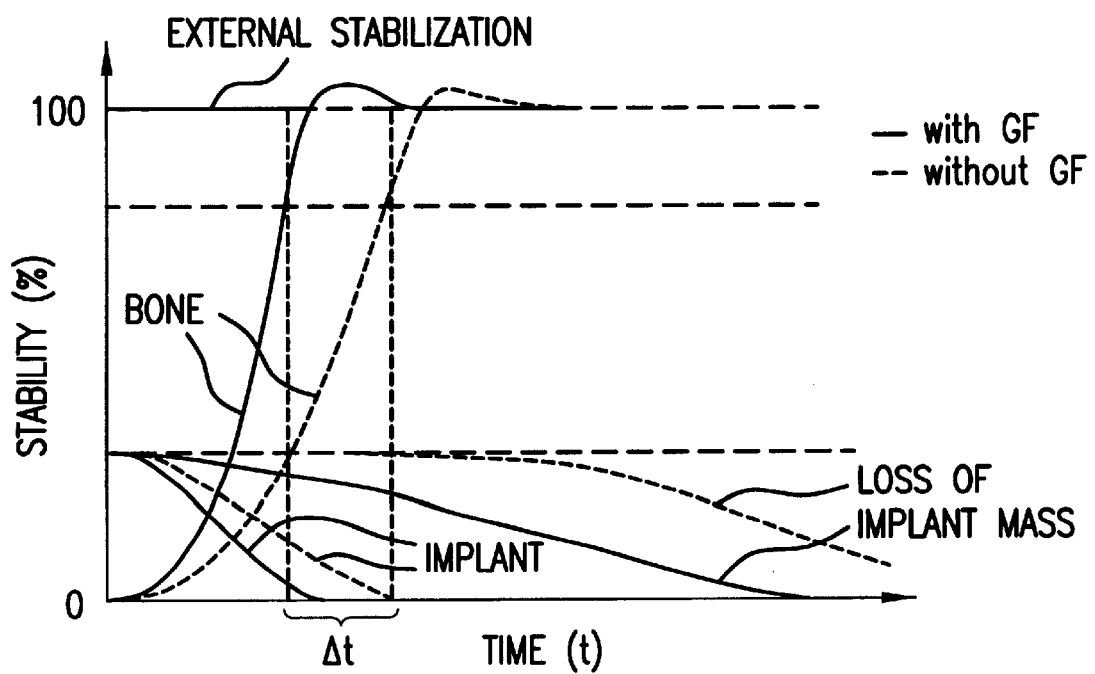
FIG. 2b is a graphical representation showing different curves identifying stability as a function of time, as related to a healing process of a fracture when using both an implant according to this invention and an additional external stabilization.

The employment of an implant in accordance with this invention with growth factors and additional external stabilization of the break is shown in FIG. 2b. One advantage of this invention is shown in FIG. 2b. In addition to the advantages described in connection with FIG. 2a, the accelerated bone healing here results in a considerable reduction $\Delta t$ of the time the external stabilization means must be worn. The earlier healing of the break and the earlier resumption of the movement of the affected area not only quite decisively reduce the period of sickness, but also quite considerably reduce the outlay in time and money necessary for follow-up treatments.

It is apparent to one skilled in the art that the teaching of this invention is not only applicable to human medicine, but that analogously this invention can also be employed by veterinary medicine in connection with all vertebrates. Ideally, the growth factors of the respective types or species of animals are used in this case.

What is claimed is:

1. In an implant having a polymeric biodegradable base material for use in reconstructive osteosynthesis and having an active ingredient which assists regeneration of bone tissue in a fracture area, wherein the polymeric biodegradable base material is formed as an osteosynthetic implant for a mechanical connection of fractured elements, the improvement comprising: the active ingredient encapsulated within a biodegradable material and forming a plurality of at least one of micro-spheres and micro-capsules embedded in the implant to assist growth in the fracture area so that a mechanical load-bearing capability of a healing fracture increases at least as fast as a load-bearing capability of the biodegradable osteosynthetic implant decreases when decomposing.

2. In the implant in accordance with claim 1, wherein the active ingredient is a combination of at least one of:

a) present in solution, b) deposited in a gel, c) linked to one of a plurality of carrier proteins and an other carrier material, d) formed as a mixture with a suitable inactive ingredient, and e) formed as a pure freeze-dried powder.

3. In the implant in accordance with claim 2, wherein a formulation of the active ingredient is injectable for application in the fracture area.

4. In the implant in accordance with claim 1, wherein the active ingredient is at least one of an epidermal growth factor (EGF), of an insulin-like growth factor (IGF), of a transforming growth factor beta (TGF-beta), of a fibriloplast growth factor (FGF), and a combination thereof.

5. In the implant in accordance with claim 1, wherein the active ingredient is a bone morphogenetic protein (BMP).

6. In the implant in accordance with claim 1, wherein the active ingredient is an insulin-like growth factor (IGF-1).

7. In the implant in accordance with claim 1, wherein the biodegradable base material is a polymer of a polylactide (PLA), a polyglycolide (PGA), a poly($\epsilon$-caprolcatone) (PCL), a poly($\beta$-hydroxybutyrate) (PHB), a poly(p-dioxanone) (PDS), and a mixture thereof.

8. In the implant in accordance with claim 1, wherein the implant is at least one of a plate, a bandage, a fabric and an element having one of a flat shape and a rod shape.

9. In the implant in accordance with claim 8, wherein the osteosynthetic implant is a connecting element in a form of one of a screw, a rivet, a pin, a nail, a spiking wire or hoop.

10. In an implant having a polymeric biodegradable base material for use in reconstructive osteosynthesis and having an active ingredient which assists regeneration of bone tissue in a fracture area, the improvement comprising: the polymeric biodegradable base material formed as an osteosynthetic implant for a mechanical connection of fractured elements, the active ingredient encapsulated within a biodegradable material and forming a plurality of at least one of micro-spheres and micro-capsules, the active ingredient spatially separated from the osteosynthetic implant, the active ingredient acting together with the implant to assist growth in the fracture area so that a mechanical load-bearing capability of a healing fracture increases at least as fast as a load-bearing capability of the biodegradable osteosynthetic implant decreases when decomposing.

11. In the implant in accordance with claim 10, wherein the active ingredient is at least one of an epidermal growth factor (EGF), of an insulin-like growth factor (IGF), of a transforming growth factor beta (TGF-beta), of a fibriloplast growth factor (FGF), and a combination thereof.

12. In the implant in accordance with claim 10, wherein the active ingredient is a bone morphogenetic protein (BMP).

13. In the implant in accordance with claim 10, wherein the active ingredient is an insulin-like growth factor (IGF-1).

14. In the implant in accordance with claim 10, wherein the biodegradable base material is a polymer of a polylactide (PLA), a polyglycolide (PGA), a poly(ε-caprolcatone) (PCL), a poly(β-hydroxybutyrate) (PHB), a poly(p-dioxanone) (PDS), and a mixture thereof.

15. In the implant in accordance with claim 10, wherein the implant is at least one of a plate, a bandage, a fabric and an element having one of a flat shape and a rod shape.

16. In the implant in accordance with claim 15, wherein the osteosynthetic implant is a connecting element in a form of one of a screw, a rivet, a pin, a nail, a spiking wire and a hoop.

17. In the implant in accordance with claim 10, wherein the active ingredient is a combination of at least one of:
  a) present in solution,
  b) deposited in a gel,
  c) linked to one of a plurality of carrier proteins and an other carrier material,
  d) formed as a mixture with a suitable inactive ingredient, and
  e) formed as a pure freeze-dried powder.

18. In the implant in accordance with claim 17, wherein a formulation of active ingredients is deposited one of in and on the osteosynthetic implants by one of:
  a) placement in one of a plurality of hollow spaces and a plurality of recesses of the osteosynthetic implants, and
  b) a plurality of adhesives.

* * * * *